US006440950B1

(12) United States Patent
Zeimer (10) Patent No.: US 6,440,950 B1
(45) Date of Patent: *Aug. 27, 2002

(54) SELECTIVE AND NON-INVASIVE VISUALIZATION OR TREATMENT OF VASCULATURE

(75) Inventor: Ran Zeimer, Reisterstown, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/676,832

(22) Filed: Sep. 29, 2000

Related U.S. Application Data (63) Continuation of application No. 09/336,895, filed on Jun. 21, 1999, now Pat. No. 6,248,727, which is a continuation of application No. 08/355,619, filed on Dec. 14, 1994, now Pat. No. 5,935,942.

(51) Int. Cl.[7] .................... A61K 31/695; A61K 31/685; A61K 31/675; A61K 9/127

(52) U.S. Cl. ............................. 514/63; 514/78; 514/79; 424/450

(58) Field of Search ............................. 514/63, 78, 79; 474/450

(56) References Cited

U.S. PATENT DOCUMENTS

| | | | |
|---|---|---|---|
| 4,579,430 A | 4/1986 | Bille | 351/206 |
| 4,801,459 A | 1/1989 | Liburdy | 424/450 |
| 4,822,335 A | 4/1989 | Kawai et al. | 604/20 |
| 4,889,129 A | 12/1989 | Dougherty | 128/664 |
| 4,891,043 A * | 1/1990 | Zeimer | 604/20 |
| 4,952,050 A | 8/1990 | Aizu et al. | 351/221 |
| 5,031,632 A | 7/1991 | Watanabe | 128/621 |
| 5,053,006 A | 10/1991 | Watson | 604/52 |
| 5,163,898 A | 11/1992 | Morcos et al. | 604/20 |
| 5,166,197 A * | 11/1992 | Kenney et al. | 514/63 |
| 5,257,970 A | 11/1993 | Dougherty | 604/20 |
| 5,266,302 A | 11/1993 | Peyman et al. | 424/9 |
| 5,279,298 A | 1/1994 | Flower | 128/633 |
| 5,707,986 A | 1/1998 | Miller et al. | 514/185 |
| 5,798,349 A | 8/1998 | Levy et al. | 514/185 |

OTHER PUBLICATIONS

Ogura et al, Investigative Opthalmology & Visual Science, vol. 32(8), 7/91, pp. 2351–2356.*
Yatvin et al, Science, vol. 202, Dec. 22, 1978, pp. 1290–1293.*
Schidt–Erfurth et al, Opthalmologe, vol. 91, pp. 789–795, 1994.*
Zeimer et al., "Noninvasive Visualization of the Primate Choriocapillary Bed and Study of its Hemodynamics," Abstract 1780; Annual Meeting of Association of Research in Vision and Opthalmology, Sarasota, FL, May 16, 1992.

Kiryu et al. (1994), "Noninvasive Visualization of the Choriocapillaris and Its Dynamic Filling" Invest. Opthal. & Visual Sci., vol. 25, No. 10, 3724–3731.
Zeimer et al. (1989), "Feasibility of Blood Flow Measurement by Externally Controlled Dye Delivery," 30 Invest. Opthal. & Visual Sci., 4:660–667.
Ogura et al. (1991), "Feasibility of Targeted Drug Delivery to Selective Areas of the Retina," 32 Invest. Opthal. & Visual Sci., 8:2351–2356.
Schmidt–Erfurth et al., (1994), "Selective Occlusion of Subretinal Neovascularization with Photodynamic Therapy," 91 Opthalmologe 6:789–795.
Asrani et al. (1995), "Systemic Toxicology and Laser Safety of Laser Targeted Angiography with Heat Sensitive Liposomes," 11 J. Ocul. Pharmacol. Ther. 4:575–584.
Asrani et al., (1995), "Feasibility of Laser Targeted Photo-Occlusion of Ocular Vessels," 79 Bri. J. Opthalm. 766–770.
Schmidt–Erfurth et al., (1995), "In Vivo Uptake of Liposomal Benzoporphyrin Derivative and Photothrombosis in Experimental Neovascularization," 17 Lasers in Surg. & Med. 2:178–188.
"Liposomes as Tools in Basic Research and Industry", Phillippot et al. (Ed.) CRS Press 1995.
Liposome Technology, 2nd Ed., vol. I, "Liposome Preparation and Related Techniques," Gregoriadis, (Ed.), CRC Press 1993.
Liposome Technology, 2nd Ed., vol. III, "Interactions of Liposomes with the Biological Milieu, " Gregoriadis, (Ed.) CRC Press 1993.
Liposome Technology, 2nd Ed., vol. II, "Entrapment of Drugs and Other Materials," Gregoriadis, (Ed.) CRC Press 1993.
"The Science of Phototherapy," Grossweiner, CRC Press 1994.
"Laser–targeted dye delivery could revolutionize visualization of choroidal new vessels," in Ocular Surgery News vol. 14, No. 12, p. 39, Jun. 15, 1996.
"Laser–targeted angiography may aid ARMD," in Opthamology Times vol. 22, No. 2, Jan. 15, 1997.

(List continued on next page.)

*Primary Examiner*—Russell Travers
(74) *Attorney, Agent, or Firm*—Testa, Hurwitz & Thibeault, LLP (57) ABSTRACT

Disclosed are methods and materials for visualizing or treating vasculature. The methods and materials in this invention relate to selective and non-invasive visualization, or treatment such as chemical occlusion, of vasculature in the mammalian eye. The methods utilize fluorescent dyes and tissue-reactive substances encapsulated within heat-sensitive liposomes which are subsequently heated to release the contents thereof at a pre-determined anatomical locus. The methods of this invention further utilize tissue-reactive agents which, when activated, are effective to cause localized tissue damage and occlusion of blood vessels and/or blood sinuses. The materials of this invention relate to diagnostic reagents and kits for visualizing or treating a mammalian blood vessel or sinus.

29 Claims, 1 Drawing Sheet

OTHER PUBLICATIONS

"Laser Targeting of Drugs to Back of the Eye" by Zeimer, 12th Nat'l Eye Research Seminar (1993).

Schmidt–Erfurth et al. (1994), "Vascular Targeting in Photodynamic Occlusion of Subretinal Vessels," Ophthalmology vol. 101, No. 12.

Asrani et al. (1997), "Feasibility of Laser–Targeted Photoocclusion of the Choriocapillary Layer in Rats," Investigative Opthamology & Visual Science, 38: 2702–2710.

Zeimer et al., "Laser Targeted Photo–Occlusion: A Potential Method to Occlude Choroidal Neovascularization," from International Symposium on Experimental and Clinical Ocular Pharmacology and Pharmaceutics, Sep. 28–Oct. 1, 1995.

"Pharmacokinetics of Heat–Sensitive Liposomes for Laser Targeted Drug Delivery" by Grebe et al., from Investigative Opthamolgoy & Visual Abstract Book—Part II, May 11–May 16, 1997.

Nishiwaki et al., "Laser Targeted Photodynamic Therapy Occludes Experimental Chordoidal Neovascularization Without Visible Damage to ROE and Choriocappilaris," from Investigative Opthamology & Visual Science, Abstract Book May 10–15, 1998.

Grebe et al., "Effects on the RPE Following Choriocapillaris Occlusion Induced by Laser Targeted Photo–Occlusion and Conventional Photodynamic Therapy," Investigative Opthamology & Visual Science, Annual Meeting Apr. 21–26, 1996.

Asrani et al. (1996), "Selective Visualization of Chorodial Neovascular Membranes," from Investigative Opthamology & Visual Science, 37:1642–1650.

Yatvin et al. (1978), Science, vol. 202, 1290–1293.

* cited by examiner

SELECTIVE AND NON-INVASIVE VISUALIZATION OR TREATMENT OF VASCULATURE

REFERENCE TO RELATED APPLICATIONS

This application is a continuation of U.S. Ser. No. 09/336,895, filed Jun. 21, 1999 now U.S. Pat. No. 6,248,727, which is a continuation of U.S. Ser. No. 08/355,619, filed Dec. 14, 1994, now U.S. Pat. No. 5,935,942.

GOVERNMENT SUPPORT

Work described herein was supported in whole or in part by Grant No. EY 07768, awarded by The National Institutes of Health. The Government has certain rights in the invention.

FIELD OF THE INVENTION

The present invention relates generally to methods and materials for visualization or treatment of vasculature.

BACKGROUND OF THE INVENTION

Of the estimated 34 million people in the United States who will be age 65 or older in 1995, approximately 1.7 million will have some visual impairment resulting from age-related macular degeneration (ARMD). Approximately 100,000 of those affected will experience a devastating, rapid loss of vision due to choroidal neovascularization (CNV). (See, for example, U.S. Dept. Health and Human Serv., (1994) National Advisory Eye Council (1990–1992).) ARMD is the most common cause of vision loss in people over age 50 and, as the population ages, a greater number of elderly persons will become blind from ARMD than from glaucoma and diabetic retinopathy combined. Leibowitz et al. (1980) 24 *Surg. Ophthalmol.* (suppl.) 335–610; Sorsby (1972) in: *Ministry of Health Reports on Public Health and Medical Subjects* (128th ed., London); Ferris (1983) 11 *Am. J. Epidemiol.* 132–4151.

Clinical research has shown that laser treatment of CNV reduces the risk of extensive scarring in selected cases of CNV characterized by a well-defined, predictable fluorescein angiographic pattern covering an area limited in size. Unfortunately, such "classic" cases comprise only 25% of the population with CNV, leaving 75% of the patients at risk of becoming blind from macular disease without the benefit of laser treatment. Moreover, the frequent (54%) recurrence of CNV is mostly attributed to incomplete angiographic visualization and subsequent inadequate treatment of CNV. Macular Photocoagulation Study Group (1986) 104 *Arch. Opthalmol.* 503–512. The practical difficulty in detecting CNV clinically has been documented in a recent study involving clinical and pathological examinations of 30 eyes. In 57% of the cases, CNV was detected histologically but not clinically. Sarks (1973) 75 *Br. J. Ophthalmol.* 587–594. This finding is in agreement with other histopathological studies in which CNV was detected in angiographically-unrecognized lesions. Bressler et al. (1992) 110 *Arch. Ophthalmol.* 827–832; Small et al. (1976) 94 *Arch. Ophthalmol.* 601–607.

As presently performed, the ability of fluorescein angiography to highlight CNV is limited by a number of factors. First, the dye rapidly fills both the retinal and choroidal vessels. Thus, visualization of small vascular beds, such as those typical of CNV, is often hampered by the lack of contrast caused by the bright fluorescence emanating from major choroidal vessels. Second, visualization of CNV is based on the leakage into and/or staining of tissue by the dye, which occurs only during a particular pathological stage. This process is not reliable because at certain stages of the disease, diseased vessels do not leak or stain. Also, metabolic waste products may accumulate in the vicinity of the lesion, decreasing the permeability or delaying the leakage into extravascular tissues. Third, when vessels leak, dye accumulates in the tissues surrounding the CNV lesion and actually masks its boundaries. Fourth, both the exciting and fluorescent light may be absorbed by subretinal blood, turbid fluid, pigment, or fibrous tissue, thereby reducing the intensity of the fluorescence emanating from the CNV. Bresler et al. (1988) 32 *Surg. Ophthalmol.* 375–413; Bressler et al. (1991) 109 *Arch. Ophthalmol.* 1242–1257.

Indocyanine green (ICG) angiography has been reportedly beneficial in some cases. Destro et al. 96 *Ophthalmology* 846–853. Because the excitation and emission wavelengths of this particular dye are longer than those of fluorescein, the light penetrates turbid media better, thereby eliminating the fourth limitation mentioned above. On the other hand, however, the enhanced penetration of light in ICG angiography aggravates the first-mentioned limitation of fluorescein angiography, i.e., interfering fluorescence, because large underlying choroidal vessels are visualized more effectively. Moreover, ICG angiography shares with fluorescein angiography the limitation of relying on leakage and staining of extravascular tissues. The poor understanding of the staining and pooling mechanisms of this dye hampers interpretation of angiograms.

The lack of adequate methods of angiographic visualization is unfortunate because clinical research has shown that laser treatment can reduce, in the long term, the risk of extensive loss of vision in classic CNV. (See, for example, Bressler et al. (1991) 109 *Arch. Ophthalmol.* 1242–1257.) In addition, the failure of laser photocoagulation has been attributed to inadequate identification of the entire extent of CNV and its location relative to the fovea.

As mentioned, CNV is commonly treated by laser photocoagulation in which a thermal scar is produced. The procedure typically causes a dramatic loss of vision when the fovea is treated. See, for example, Macular Photocoagulation Study Group (1991) 109 *Arch. Ophthalmol.* 1220–1231. Nonetheless, the treatment is performed to prevent progressive visual loss. The cases eligible for treatment, which make up only 25% of the eyes with CNV, must be the well-defined "classic" type of CNV that is not too large. The remaining 75% of affected eyes are untreated because laser photocoagulation does not spare useful vision. In addition, new blood vessels recur in a majority of the patients (54%) treated with laser photocoagulation, thereby necessitating further scarring treatment. Other than the incomplete identification of CNV mentioned above, recurrence has been attributed to damage to Bruch's membrane and scarring, conditions known to predispose tissues to new blood vessel growth.

It is an object of this invention to provide methods and materials for selective occlusion of vasculature. That is, it is an object of this invention to provide for the occlusion of blood vessels without significant, concomitant damage to tissue surrounding and supplied by said blood vessels. It is another object of the instant invention to provide methods and materials for selective and non-invasive chemical occlusion of blood vessels and sinuses in the mammalian eye, especially blood vessels and sinuses of choriodal origin. It is a further object of the instant invention to provide methods for selectively and non-invasively occluding vascular abnormalities of the mammalian eye, such abnormalities being associated with macular degeneration and related clinical conditions involving neovascularization, such as choroidal neovascularization. It is still a further object of the instant invention to provide methods for non-invasively occluding vascular abnormalities associated with pathologies of the choriocapillaris such as choroideremia, gyrate atrophy, and acute placoid multifocal pigment epitheliopathy, as well as vascular abnormalities which are non-choroidal such as those associated with diabetes. It is yet another object of the instant invention to provide diagnostic reagents and diagnostic kits for selective, non-invasive chemical occlusion of vasculature. These and other objects and features of the invention will be apparent from the description, drawings and claims which follow.

SUMMARY OF THE INVENTION

The present invention provides a method of chemically occluding a blood vessel or blood sinus in a mammalian eye which involves: co-administering intravenously a fluorescent dye encapsulated within heat-sensitive liposomes and a tissue-reactive agent which is effective to cause chemical tissue damage following its activation; non-invasively heating tissue at a pre-determined anatomical locus within the eye so that the heat-sensitive liposomes leak and release their contents into the blood vessel or sinus at the pre-determined locus; exciting the fluorescent dye; visually observing a pattern of fluorescent vasculature which develops at the pre-determined locus; and, activating the tissue-reactive agent disposed within the blood vessel or sinus so that the blood vessel or sinus is chemically damaged to an extent sufficient to occlude the vessel or sinus. As used herein, the steps of the method of the instant invention are collectively referred to as "laser-targeted occlusion." In some cases, the steps which precede activation of the tissue-reactive agent are collectively referred to as "laser-targeted angiography," "laser-targeted delivery," or "laser-targeted visualization." The present invention contemplates that the steps of the method of laser-targeted occlusion can be repeated for an amount of time that the liposomes are circulating systemically following their administration. Similarly, the present invention contemplates that the steps of laser-targeted angiography can be repeated for an amount of time that the liposomes are circulating systemically following their administration.

In another embodiment of the method of the instant invention, the method of chemically occluding a blood vessel or sinus in a mammalian eye involves: co-administering intravenously a fluorescent dye and a tissue-specific factor co-encapsulated within heat-sensitive liposomes, said tissue-specific factor being effective to impair growth or regeneration of vasculature; non-invasively heating tissue at a pre-determined anatomical locus within the eye so that the heat-sensitive liposomes leak and release their contents into the blood vessel or sinus at the pre-determined anatomical locus; exciting the fluorescent dye; visually observing a pattern of fluorescent vasculature which develops at the pre-determined anatomical locus; and, exposing the blood vessel or sinus at the locus to the tissue-specific factor disposed within the blood vessel or sinus so that the growth or regeneration of the blood vessel or sinus is impaired.

In yet another embodiment, the instant invention provides a method of occluding vasculature in a mammalian eye which involves: administering intravenously heat-sensitive liposomes having a fluorescent dye encapsulated therein; irradiating a pre-determined anatomical locus within the eye with a first laser beam to selectively and non-invasively heat the vasculature at the locus so that the liposomes accumulated at the locus release their contents into the vasculature at the locus; identifying a blood flow origin within the vasculature by visualizing an advancing blood/dye boundary within a feeder blood vessel that supplies blood to a vascular abnormality at the locus; and, occluding the feeder blood vessel with a second laser beam focused on the blood/dye boundary.

In another aspect, the invention features materials for use in the method, e.g., a diagnostic reagent and a diagnostic kit each comprising a fluorescent dye encapsulated within heat-sensitive liposomes and a tissue-reactive agent. Alternatively, the diagnostic reagent and kit each comprise a tissue-reactive agent co-encapsulated with fluorescent dye within heat-sensitive liposomes. In yet another embodiment, the instant invention contemplates that the diagnostic reagent and kit each comprise a fluorescent dye which is a tissue-reactive agent. The diagnostic kit of the instant invention optionally further comprises means for encapsulating fluorescent dye, either alone or together with tissue-reactive reagent, within heat-sensitive liposomes.

The method of laser-targeted angiography and occlusion of the instant invention solves problems encountered in conventional fluorescein or ICG angiography. For example, the local selective release of a fluorescent dye according to the method of the instant invention permits pre-determined vascular beds to be visualized without interference from fluorescence emanating from overlying or underlying beds. Second, visualization according to the instant invention is independent of staining and leakage of dye into tissue surrounding a region of abnormal vasculature, such as choroidal neovascularization (CNV). Rather, it relies solely on the presence of a dye in the vascular lumen. Thus, the CNV can be visualized as long as it is patent, i.e., open to blood flow. This feature also simplifies interpretation of angiograms. Third, the short time during which release of the encapsulated dye occurs, accompanied by rapid and eventual clearance thereof, ensures that the dye does not accumulate outside the vessels, and thus does not mask the CNV as do conventional materials and methods. Fourth, the hemodynamics of the CNV, delineated by the progress of the dye, using the methods of the instant invention, allow the vessels feeding the CNV to be identified. Such identification allows the clinician to selectively occlude an identified feeder vessel. In this manner, large areas of retina overlaying the CNV could be spared, thus limiting the unnecessary visual loss typically associated with prior art methods of photocoagulation. Fifth, angiograms performed in accordance with the instant invention can be repeated for at least about 45 minutes as long as the liposomes are circulating in the blood. This provides opportunities to correct errors in alignment of optical equipment and to perform angiography of both eyes during the course of a single patient visit and/or single therapeutic procedure.

All the above advantages can be demonstrated using the methods and materials of the instant invention which permit successful visualization of classic and occult CNV, as well as visualization of the choriocapillaris, even in the presence of scar tissue. Laser-targeted angiography as described herein detects and delineates CNV and CNV-type lesions effectively. This increases the number of patients who could benefit from such therapy, reduce the recurrence rate now attributed to lack of adequate visualization, and restrict the treated area, thereby reducing the amount of visual loss accompanying occlusion treatment.

As disclosed herein, a method of occluding CNV that does not cause a scar and spares the overlying retina and adjacent choriocapillaris is highly desirable and can be met by the instant invention's methods of laser-targeted occlusion. In one embodiment, the method of the instant invention combines laser targeted delivery and photodynamic therapy by targeting delivery of a photosensitive agent to the CNV and occluding the CNV by photosensitization of the agent. Such a method solves many of the limitations of systemic photodynamic therapy and those of conventional thermal laser photocoagulation. Thus, the tissue-reactive agent can be released specifically in the choroid, thus avoiding release in the retinal vessels. Similarly, the agent also can be released within the CNV while avoiding release in the retina. Next, by irradiating only after the agent's release into the pre-determined anatomical locus, tissue damage can be limited essentially to the vessels that are selectively perfused by the agent. The lack of accumulation of the agent in the interstitial tissues prevents their subsequent damage upon activation. Third, as disclosed herein, there are clear indications that CNV's are perfused by a slower blood flow than the normal choriocapillaris. Therefore, the agent could be released and the tissue irradiated only after enough time has elapsed to ensure clearance from the normal choriocapillaris. This sequence would preclude damage to the choriocapillaris which is crucial to the maintenance of the retinal pigment epithelium. Fourth, laser-targeted occlusion of CNV according to the instant invention allows both "classic" and "occult" type lesions to be amenable to treatment, as the skilled practitioner now can selectively occlude the CNV while sparing the retina and thus preserving vision. Fifth, laser-targeted occlusion does not cause a scar as does thermal occlusion, thereby reducing risk of recurrence of neovascularization.

The foregoing and other objects, features and advantages of the present invention will be made more apparent from the following detailed description of preferred embodiments of the invention.

BRIEF DESCRIPTION OF THE DRAWINGS

The foregoing and other objects and features of this invention, as well as the invention itself, may be more fully understood from the following description, when read together with the accompanying drawings, in which.

DETAILED DESCRIPTION OF PREFERRED EMBODIMENTS

Figure 1:
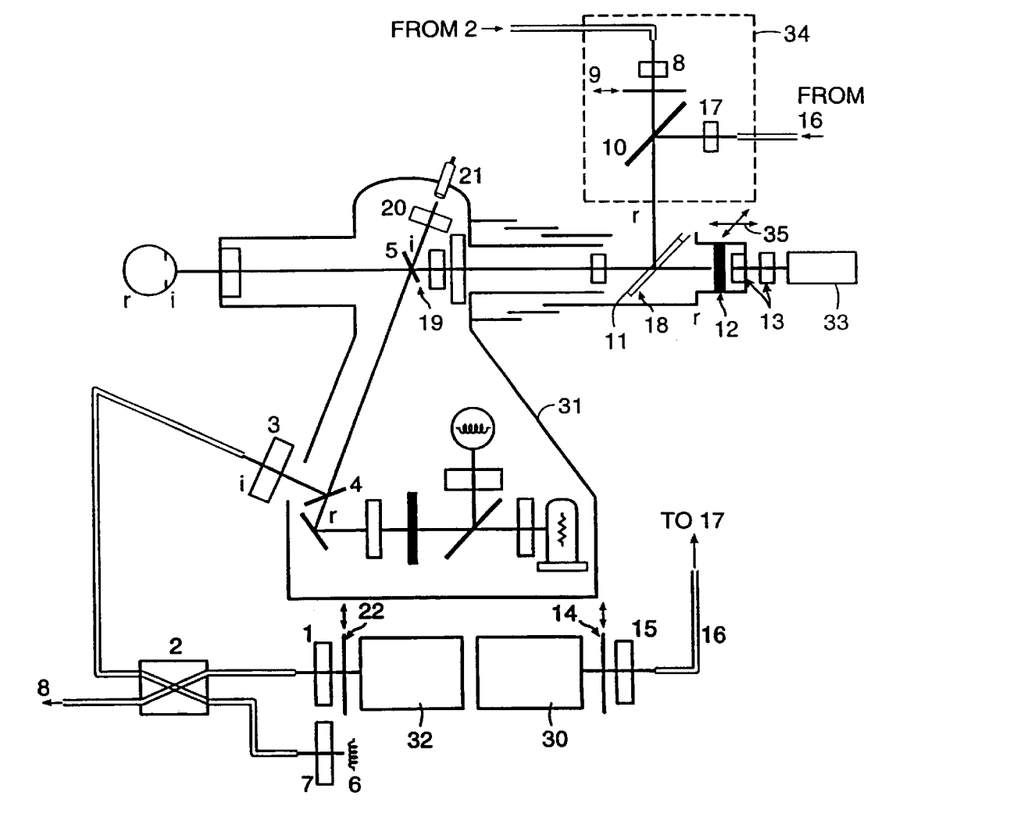
The FIGURE is a diagrammatic representation of the instrumentation used to perform laser-targeted angiography and occlusion.

As will be described below in greater detail, the instant invention relates to methods and materials for occluding vasculature. Specifically, the methods and materials of the instant invention relate to selective and non-invasive chemical occlusion of vasculature in the mammalian eye. The methods utilize fluorescent dyes and tissue-reactive substances encapsulated within heat-sensitive liposomes. These liposomes are subsequently heated to release the contents thereof at a pre-determined anatomical locus. The methods of this invention further utilize tissue-reactive agents which, when activated, are effective to cause localized tissue damage and occlusion of blood vessels and/or blood sinuses. The materials of this invention relate to diagnostic reagents and kits for identifying and chemically occluding a mammalian blood vessel or sinus.

As used herein, the term "occluding" means obstructing blood flow in a blood vessel or sinus. The term "occlusion" means a physical blockage or impediment in a blood vessel or sinus that obstructs passage of blood therethrough. An occlusion can develop immediately as the direct result of treatment, or it can gradually develop as a consequence of an earlier treatment. Occlusion can occur when there is an impenetrable blockage in an existing vessel or sinus, or as a result of treatment which subsequently impairs the growth or regeneration of a blood vessel or sinus. Occlusion of vasculature can be caused chemically or thermally, as desired. As used herein, an occlusion may be either permanent or temporary.

The term "chemically occluding" means any non-thermal means of occluding. Chemical occlusion is the result of treatment of vasculature with a chemical, biological, pharmaceutical, or pharmacological agent which causes physiological and/or structural damage to vasculature. For example, "chemical damage" means damage caused by toxic radicals, cross-linking radicals or the equivalents thereof; damage caused by biological moieties which bind, interact with, or otherwise affect vascular integrity and/or modulate vascular growth or regeneration; or, damage caused by pharmaceutical or pharmacological compounds such as a vasoconstrictor or a vasodilator. "Tissue damage" refers to damage to blood vessel or blood sinus tissue originating within the lumen, such as originating within the endothelial cell lining of the lumen, and which subsequently progresses into an occlusion. Tissue damage can be caused chemically as described above or thermally such as with a laser beam. "Interstitial tissue" refers to non-vascular tissue, e.g., retinal or subretinal tissues surrounding and supplied with nutrients by blood vessels.

As used herein, the term "administration" or "co-administration" is intended to mean any form of delivery into a recipient's blood supply, such as by intravenous injection or infusion. The only modes of delivery excluded from use in the instant invention are those which damage the capsular integrity of liposomes and/or cause the liposomes' contents to be released prematurely, i.e., prior to the intentional release of their contents by heating as described herein.

As used herein, the term "fluorescent dye" is intended to mean any fluorescent substance suitable for use in the instant invention. As will be understood by the skilled practitioner, fluorescent substances suitable for use in the instant invention include those which are suitable for administration to mammals, including humans. It will be further understood that fluorescent substances amenable to encapsulation, or which can be rendered amenable to encapsulation, are suitable for use in the instant invention. Moreover, substances whose fluorescence is quenched when in an encapsulated form at an appropriate concentration as described herein also are suitable for use in the methods and materials of the instant invention. Thus, dyes such as 6-carboxyfluorescein and similar fluorescein derivatives are suitable for use herein. Particularly useful fluorescent substances are those which can be excited by and emit light at wavelengths not strongly absorbed by opaque tissue lesions, blood and/or biological pigments. Such substances readily can be detected in eye tissue comprising lesions, blood or biological pigments. In this regard, indocyanine green (ICG) also is suitable because its excitation is not strongly absorbed by opacities, blood, or biological pigments. Similarly, aluminum phthalocyanine tetrasulfonate (AlPcS$_4$) is an exemplary fluorescent substance and tissue-reactive agent for the reasons discussed herein below, however, other equivalent substances would also be suitable. Identification of equivalents is well within the skill of the ordinary practitioner and would require no more than routine experimentation.

As used herein, the term "tissue-reactive agent" is intended to mean an agent competent to react adversely with vascular tissue such that the vascular tissue is chemically damaged. Tissue-reactive agents include those competent to generate upon activation toxic radicals or cross-linking substances which physiologically and/or structurally damage vascular tissue. For example, tissue-reactive agents can preferentially interact with tissue components disposed on the inner lumen walls of mammalian vasculature; interaction with these lumen components results in an adverse effect on the associated vasculature which progresses into an occlusion. Additionally, tissue-reactive agents can be photosensitive agents activated by light to produce tissue damage. An example of one such photosensitive agent useful in the method of the present invention is aluminum phthalocyanine tetrasulfonate. "Tissue-reactive by-products" refer to the activation by-products of tissue-reactive agents which may form within the vasculature following activation and act chemically to damage the vascular tissue.

As used herein, the term "heat-sensitive liposomes" includes liposomes formulated using physiologically compatible constituents, such as dipalmitoylphosphatidylcholine and dipalmitoylphosphatidyl-glycerol phospholipids, that permit preparation of liposomes using art-recognized techniques that release their contents at temperatures above those of the mammalian body temperature, i.e., above 37° C. Upon exposure to temperatures at least about 4° C. above mammalian body temperature, "release" occurs by leakage or seepage of the liposomes' contents or by actual lysis (complete or incomplete) of the liposomes. The instant invention contemplates use of heat-sensitive liposomes which are negatively-charged unilamellar liposomes less than about 450 nm in diameter to facilitate handling, administration, unhindered progress through mammalian vasculature, and minimize side effects, e.g., interference with the mammalian blood clotting cascade.

The method of the instant invention features, in certain embodiments, heat-sensitive liposomes which contain a quenching concentration of fluorescent dye. The term "quenching concentration" refers to that concentration of dye which is sufficiently high to mask or minimize detection of fluorescence even when illuminated with a suitable light source. The physics of fluorescence quenching are well-known in the art and the skilled artisan would be able to determine a quenching concentration for any fluorescent dye through no more than routine experimentation. When the heat-sensitive liposomes used in the methods of the instant invention are heated, the contents of the liposomes leak into and/or are released into the lumen of the blood vessels in which they have accumulated, thereby causing a dilution in the concentration of the fluorescent dye by the plasma within the vessels which results in a non-quenching concentration of dye, e.g., a concentration that visibly fluoresces upon sufficient excitation with a suitable light source.

As used herein, the term "non-invasively heating" means heating without causing substantial damage to tissue, including scarring or physiological impairment. Non-invasive heating as accomplished by the instant invention typically involves irradiating tissue with a laser beam at a pre-determined depth by manipulating wavelength and pulse duration. Methods of the instant invention contemplate a laser for non-invasively heating which has a wavelength absorbed by blood and ocular pigments. According to a preferred embodiment of the instant invention, a blood vessel or sinus is selectively and non-invasively heated to a temperature of approximately 41° C. by irradiating with a laser beam having a wavelength absorbed by blood, for example, 488 nm. Such non-invasive heating by irradiating tissue with a suitable laser beam pre-disposes the heat-sensitive liposomes of the instant invention to release their contents into the vasculature at the tissue locus without causing substantial damage to the vascular and extravascular (interstitial) tissue at that locus or elsewhere, while minimizing heating of extravascular tissue elsewhere.

As used herein, the phrase "pattern of fluorescent vasculature" means the hemodynamic distribution of fluorescence which develops at a pre-determined anatomical locus immediately following release and excitation of the fluorescent dye at the locus. The vasculature subject to selective heating displays a distribution of fluorescence which delineates the topology of the vasculature at the locus. The display changes as the fluorescence advances downstream or upon the end of the release, as fresh blood not carrying released fluorescence flows into the locus. A pattern as contemplated by the instant invention includes not only this time-dependent feature, but also includes vasculature-dependent features. An exemplary vasculature-dependent feature involves the differential distribution of fluorescence in normal blood vessels versus abnormal blood vessels. Fluorescence will clear from blood vessels with normal blood flow earlier than from those blood vessels with subnormal blood flow. Thus fluorescence persists in vessels with sub-normal blood flow. Such abnormal blood vessels, therefore, display a delayed clearance of the released dye. Patterns of fluorescent vasculature developed through practice of the methods described herein can therefore be used to identify a vascular abnormality and/or implement occlusion of such an abnormality. For example, the pattern of fluorescence which develops according to the instant methods may be a pattern of vasculature originating from the choroid. An abnormal blood vessel or sinus with persistent fluorescence may be an abnormal choroid blood vessel or sinus associated with choroidal neovascularization. Another important feature of the pattern of the instant invention is that it is relatively visually unimpaired by fluorescence emanating from overlying or underlying vascular beds. This is so because the method of the instant invention permits selective release of fluorescent dye at a pre-determined anatomical locus, thereby avoiding confounding fluorescence in adjacent vascular beds. In the case of a pattern emanating from the choroid, interference by vessels of the retina and the large choroidal vessels is substantially eliminated by the methods of the instant invention.

The methods of the instant invention are suitable for occluding a vascular abnormality. A "vascular abnormality" refers to, for example, a physiologically atypical vascular feature, including structural as well hemodynamic abnormalities. A vascular abnormality may be the consequence of a congenital or developmental irregularity, an injury, a disease, a neoplasm, or aging. Often, it is associated with vision impairment or loss. Macular degeneration is a vascular abnormality particularly suitable for occlusion by the methods and materials of the instant invention. In particular, choroidal neovascularization (CNV), including classic and occult choroidal neovascularization, can be occluded using the methods and material of the instant invention. Additionally, a vascular abnormality refers to a pathology of the choriocapillaris such as choroideremia, gyrate atrophy, acute placoid multifocal pigment epitheliopathy, and the like. Moreover, the methods and materials of the instant invention are suitable for occlusion of vascular abnormalities associated with other disease such as diabetes which affect non-choroidal vasculature.

As used herein, the term "activating" or "activation" is intended to mean the process by which the tissue-reactive agent is induced or stimulated to effect chemical damage and occlusion of vasculature. The exact manner in which an activated tissue-reactive agent effectuates this chemical damage and occlusion depends on the type of tissue-reactive agent used. For example, a tissue-reactive agent may be chemically inert or non-reactive until it is exposed to an activating process such as irradiation with a suitable laser beam. In one embodiment of the instant invention, the tissue-reactive agent is activated by irradiating the blood vessel or sinus at a pre-determined anatomical locus with a laser beam, the wavelength of which being sufficient to activate the agent. A wavelength suitable for use in the instant invention is one which sufficiently activates the tissue-reactive agent and does not itself cause substantial damage to tissue at the pre-determined anatomical locus. For example, when aluminum phthalocyanine tertrasulfonate is used as the tissue-reactive agent in the method of the instant invention to occlude CNV-type vasculature, irradiation of the vasculature with a laser wavelength of approximately 675 nm is sufficient to cause activation of the agent. The photoactivated agent then causes chemical tissue damage which results in occlusion. Thus, the term activation contemplates any process by which an agent is selectively stimulated or induced to manifest certain properties which lead to occlusion as that term is defined herein. In accordance with the methods of the instant invention, activation preferably is accomplished after clearance of the fluorescent dye and the agent from vasculature with normal blood flow, and before clearance of the dye and the agent from vasculature with subnormal blood flow. Alternatively, activation and release of the agent may occur simultaneously rather than sequentially. In this particular embodiment, activation is preferably accomplished before observable leakage of the dye or agent into tissue adjacent a particular blood vessel or sinus, or before significant observable clearance of the dye or agent from the site of their release from the heated liposomes. The terms "normal blood flow," "sub-normal blood flow," and "clearance" as used herein are defined below. "Normal blood flow," refers to the movement of blood through mammalian vasculature which is unimpeded and progressing under physiologically-normal pressures and at physiologically-normal rates. Normal blood flow may be found in blood vessels having mature diameters. "Subnormal blood flow" refers to the movement of blood through mammalian vasculature which is not progressing at physiologically-normal rates, and perhaps also not progressing under physiologically-normal pressures. Sub-normal blood flow may result from a stricture in the vasculature caused by disease, or may be associated with damage or disease in adjacent vasculature. Sub-normal blood flow may also be the result of blood vessels having immature diameters, tortuous paths or excessive length, such as newly formed blood vessels. "Clearance" refers to the disappearance of, or diminishment of, an agent released in the blood vessels and/or vasculature at a particular anatomical locus. Typically, clearance is associated with displacement, by fresh filling blood, of the blood into which the agent had been released earlier. For example, clearance is observed upon the diminishment of the fluorescence emitted by the fluorescent dye.

In a currently preferred embodiment of the method of the instant invention, the method of selective and non-invasive laser-targeted occlusion involves: administering intravenously heat-sensitive liposomes having encapsulated within a tissue-reactive agent and a fluorescent dye; irradiating a pre-determined anatomical locus within the eye with a first laser beam so that vasculature at the pre-determined locus is selectively and non-invasively heated and the heat-sensitive liposomes accumulated at the locus leak and release their contents into the vasculature at the locus; exciting the released fluorescent dye; monitoring clearance of the fluorescent dye from blood vessels with normal blood flow while simultaneously monitoring persistence of the dye within blood vessels having subnormal blood flow so that a vascular abnormality can be visualized at the pre-determined anatomical locus; and, irradiating with a second laser beam the blood vessels with subnormal blood flow by focusing the second laser on vessels containing persistent fluorescent dye so that the tissue-reactive agent also persisting in such vessels is activated, resulting in chemical damage to and occlusion of the blood vessels with subnormal blood flow. As used in this preferred embodiment, "a first laser beam" refers to a laser beam having a wavelength absorbed by blood and ocular pigments. Additionally, a first laser beam contemplates one which selectively heats tissue, including its blood vessels or sinuses, to a temperature of approximately 41° C. without causing substantial physiological damage to that tissue or vasculature. As used in this preferred embodiment, "a second laser beam" refers to a laser beam which is suitable to activate the tissue-reactive agent without causing substantial physiological damage to the vasculature in which it is disposed. Further, the second activating laser beam causes minimal damage to adjacent extravascular (interstitial) tissue.

As used herein, the terms "persistence" and "clearance" are relative terms intended to mean lingering, detectable fluorescence versus fluorescence which disappears and/or diminishes (in a time-dependent manner, e.g., synchronized with the cardiac cycle) to the extent that its detection quickly becomes negligible. Normal blood flow may be associated with vasculature which exhibits early clearance while subnormal blood flow may be associated with vasculature which exhibits lingering, persistent fluorescence and delayed clearance. As discussed above, the methods of the instant invention effectively exploit this fluorescent differential to identify normal and non-normal vasculature. Thus, the step of the instant invention relating to activating the tissue-reactive agent preferably is accomplished after clearance of the dye and the agent from vessels with normal blood flow, and before clearance from vessels with subnormal blood flow.

In accordance with the embodiments discussed above, the method of the instant invention involves encapsulating substances in artificial lipid vesicles called liposomes, injecting them intravenously, and releasing their contents in the selected tissue by non-invasively heating the blood vessels therein. Using these embodiments of the instant method, for example, dyes and tissue-reactive agents can be released into a specific portion of the subretinal choroidal vasculature to enable visualization of the choriocapillaris even in the presence of subretinal lesions, without relying on leakage or staining.

To enhance the specificity of release of the dye and tissue-reactive agent into the choroidal vasculature, for example, the heat must be concentrated maximally in the region of interest. Heat or laser-energy absorbing substances in this region are blood, waste products, occasionally extravasated blood, the retinal pigment epithelium (RPE) and the choriocapillaris. In the case of a choroidal disease such as CNV, the CNV is about 20 µm thick and the choriocapillaris is of a similar thickness. By matching the heating laser wavelength to an absorption peak of blood or ocular pigments, most of the energy is deposited in the region of interest. At about 488 nm, the RPE absorbs the fist 40 to 75% of the light, and the CNV absorbs 25% of the remaining light. Thus, even without taking into account the absorption of the waste products, 55 to 81% of the energy is absorbed. The presence of a minimal amount of extravasated blood (50 µm thick) is sufficient to leave an insignificant amount of energy beyond the RPE. In areas void of CNV, for example, the RPE and the choriocapillaris absorbs 55% to 81% of the energy, thus also letting little light penetrate into the choroid. In other words, most of the energy is deposited within 20 µm of the RPE.

Upon heating, the temperature distribution inside a retinal region overlaying an area of RPE heated by approximately 4° C. can be calculated from well-established first principles. For a heated disc 800 µm in diameter, the rise in retinal temperature is about 2.8° C. at a distance of 150 µm, i.e., where the first retinal capillaries are located. This indicates that the temperature rise in the tissue surrounding the retinal vessels is not sufficient to cause heating of liposomes and release therefrom in retinal capillaries. Retinal vessels (typically 50 µm or less in diameter in the central macula) absorb some light but this only causes a heat rise of less than about 0.50° C.

Thus a CNV and its vicinity will reach the releasing temperature of the liposomes while the retinal tissues will not. Consequently, releasing substances such as dyes and tissue-reactive agents in the choroid, but not releasing in the retina can be accomplished using the methods and materials of the instant invention.

In accordance with the instant invention, the fluorescent dye released into a CNV and the choriocapillaris, for example, yield a laser-targeted angiogram permitting visualization of the vasculature at a pre-determined anatomical locus. During the early phases of the release, released substances fill the vessels at the locus. Fluorescence and tissue-reactive agents subsequently clear from the choriocapillaris in approximately 120–240 msec. As disclosed herein, clearance from vasculature associated with CNV or a CNV-type lesion is delayed. This is based, in part, on the fact that the path from the level of the choriocapillaris to the CNV and back to the choriocapillaris is longer than the 270 µmeter diameter of a choroidal lobule within the underlying and/or surrounding choriocapillaris. The circuit of flow of blood in the CNV is in parallel with that of the circuit of flow in the choriocapillaris. Thus the delayed clearing of vasculature associated with a CNV-type lesion permits hilighting of the lesion after the fluorescence has cleared from the underlying and surrounding choriocapillaris when the methods and materials of the instant invention are utilized. In essence, this means that fluorescence will remain for a longer period of time within the CNV-type lesion, thereby permitting the practitioner to precisely delineate and localize the site of the CNV lesion and occlude the vasculature, for example, by activating the tissue-reactive agent also persisting at the site.

One preferred embodiment of the present method relies on instrumentation such that release of fluorescent dye and tissue-reactive/photosensitive agent from the heat-sensitive liposomes is accomplished with an argon laser at 488 nm and activation of the tissue-reactive agent is accomplished with a laser diode at 675 nm. Use of two separate lasers allows delay of activation after the agent's release and only until the agent has cleared from the choriocapillaris. This enhances the damage to the CNV while minimizing the effect on the choriocapillaris. In another embodiment, release and activation of the tissue-reactive agent can be accomplished simultaneously with the same laser beam. To titrate the power of the laser and ensure that the agent is being released, the instant invention contemplates fluorescent dye in liposomes injected simultaneously with the agent; laser-targeted angiography according to the present invention is then used to visualize the agent's release. The actual anatomical area covered by the activating beam is tailored in size and depth to the anatomical area of the CNV perfused by the agent.

As illustrated in the Figure, the light for activation of the tissue-reactive agent originates from a diode laser 30 operating at approximately 675 nm. The laser output is focused into a fiber 16 by an optical coupler 15. The output of the fiber is collimated by a lens 17 and diverted toward a fundus camera 31 by a dichroic mirror 10 reflecting in red. A second mirror 18 then directs the beam into the imaging path of the camera. The desired size of the beam is obtained by selecting the numerical aperture of the fiber and the focal length of the collimating lens. The power and the duration of the activating pulse will be controlled from a computer via the analog input port of the diode laser console. In addition, a hard-wired shutter 14 with a fixed delay will ensure limited exposure should the computer malfunction. The power of the activation beam is also monitored by a photosensor 21. A more detailed description of the instrumentation suitable for use in the instant invention, and its application in the methods of the instant invention, follows below in Example 1.

In operation, laser-targeted angiography in accordance with the present invention may be performed first, without use of a second laser. The preferred image acquisition and processing routines allow immediate feedback on the location of the CNV. The time necessary to allow clearance of the dye from normal vessels can be assessed, first manually, and then, numerically from the angiograms. The subsequent steps then consist of releasing the contents of the liposomes and turning the excitation laser on after the predetermined delay.

Yet another embodiment of the method described herein further comprises co-administering a tissue-specific factor encapsulated within heat-sensitive liposomes which is effective to impair growth or regeneration of a blood vessel or blood sinus. In a preferred embodiment, the instant invention provides a method of chemically occluding a blood vessel or blood sinus including the step of co-administering intravenously a fluorescent dye and a tissue-specific factor, both of which being encapsulated within heat-sensitive liposomes. The term "tissue-specific factor" means any moiety which manifests an affinity for vascular tissue and/or its individual components and affects said tissue adversely, such as by causing tissue damage, inhibiting tissue growth or inducing tissue regression in vasculature. Moreover, it is further contemplated that a tissue-specific factor is one which binds to endothelial cell receptors of a growing or regenerating blood vessel or blood sinus. In the instant invention, a tissue-specific factor may be an antibody such as an antibody directed against vascular endothelial growth factor or fibroblast growth factor. Impairment of growth or regeneration refers to a disruption in the normal growth or reparative processes usually exhibited by vascular tissue; the disruption may be permanent or temporary.

Additionally, the laser-targeted occlusion method of the instant invention may further comprise co-administering an anti-inflammatory agent or an antibiotic encapsulated within heat-sensitive liposomes. Antibiotic is understood to include anti-bacterial, anti-fungal, anti-neoplastic and anti-parasitic antibiotics. Anti-neoplastic antibiotics include, but are not limited to, the aclacinomycins, bleomycins, chromomycins, mitomycins, and the olivomycins (see the *Merck Index,* 11th edition, 1989).

In yet another embodiment, the instant invention provides a method of occluding vasculature in the mammalian eye involving the steps of: administering intravenously heat-sensitive liposomes having encapsulated within a fluorescent dye; irradiating a pre-determined anatomical locus within the eye with a first laser beam in order to selectively and non-invasively heat the vasculature and cause the liposomes accumulated therein to release their contents; identifying abnormal blood vessels or sinuses and a blood flow origin within abnormal vasculature by visualizing an advancing blood/dye boundary within the feeder vessel supplying blood to the vascular abnormality; and, occluding the feeder blood vessel with a second laser beam focused on the blood/dye boundary. The term "blood/dye" boundary describes an interface, i.e., a discernible point of distinction, between non-fluorescent filling blood, i.e., freshly entering blood devoid of released dye, and draining blood, i.e., fluorescent blood into which dye and/or tissue-reactive agents had been earlier released. The blood/dye boundary need not be sharply delineated to be successfully identified and localized. It is enough for practice of the methods described herein that this boundary signifies a relative separation of filling blood and draining blood. A "feeder blood vessel" refers to a vessel or complex of vessels which supplies blood to a particular system of vasculature at a particular anatomical locus. A feeder blood vessel may supply a normal vascular system with blood, or alternatively it may supply an abnormal vascular system with blood. This particular embodiment of the invention contemplates at least two different modes of occlusion using a second laser beam. The first mode involves a second heating laser beam which is effective to cause heat damage to the feeder blood vessel such that the vessel is coagulated and occluded. "Heat damage" means thermally-induced damage such as by laser burning. "Coagulated" or "coagulation" refers to the physiological condition of a heat-damaged vessel following laser burning. In this first mode, occlusion is the result of deliberate heat damage, but the heat damage is confined to the blood/dye boundary. In contrast, a second mode of occlusion contemplates a tissue-reactive agent which, upon irradiation with a second activating laser beam focused on said blood/dye boundary, causes chemical damage to the vasculature tissue so it becomes occluded; this particular mode does not cause heat damage or coagulation.

In another aspect, the instant invention further provides a diagnostic reagent for identifying and chemically occluding a blood vessel or blood sinus in a mammal. The diagnostic reagent comprises a fluorescent dye encapsulated within heat-sensitive liposomes; a tissue-reactive reagent effective upon activation to cause chemical damage to tissue; and, a pharmaceutically acceptable vehicle. "Pharmaceutically acceptable vehicle" refers to any vehicle which is suitable for systemic administration to a mammal, particularly administration into the blood stream. Thus, for example, a suitable vehicle is a physiologically balanced, aqueous salt solution. In another embodiment, the tissue-reactive agent is encapsulated within heat-sensitive liposomes, either alone or together with the fluorescent dye. In yet another embodiment, the fluorescent dye also is the tissue-reactive agent.

The instant invention also provides a diagnostic kit for identifying and chemically occluding a blood vessel or blood sinus in a mammal. The diagnostic kit of the instant invention comprises a fluorescent dye; a tissue-reactive agent effective upon activation to cause chemical damage to tissue; and, means for encapsulating said dye within heat-sensitive liposomes. In another embodiment, the kit comprises an additional means for encapsulating the tissue-reactive agent within heat-sensitive liposomes, either alone or together with the fluorescent dye. In yet another embodiment, the tissue-reactive agent and the fluorescent dye are the same. As used herein, the term "means for encapsulating" refers to any means suitable for encapsulating the above-described components within heat-sensitive liposomes as defined herein. The means may be in desiccated form, dehydrated form, or otherwise in non-liquid form. If non-liquid means are provided, the diagnostic kit of the instant invention optionally further comprises a suitable rehydrating reagent. Alternatively, the means may be in liquid form, ready-to-use, or may require pre-mixing. Preparing liposomes such as those used in the instant invention is well-known in the art and the skilled artisan would be able to devise such encapsulating means through no more than routine experimentation.

Practice of the invention will be still more fully understood from the following examples, which are presented herein for illustration only and should not be construed as limiting the invention in any way.

EXAMPLE 1

Instrumentation. Image Acquisition, and Image Processing

EXAMPLE 1.1

Delivery of Liposome Release Beam

A suitable delivery means consists of an argon laser for the release.

The releasing beam is delivered through the illumination arm of a fundus camera (Zeiss). In this camera, the illumination path is designed to deliver an annulus of light at the pupil plane leaving the center unexposed to light and reserved for the imaging path. When the pupil is large the illumination path is unobstructed but, if the pupil is partially dilated, or if a small animal is examined, the iris blocks part of the illumination. Clipping by the iris hinders the constant and predictable delivery of power through the releasing beam. To overcome this limitation, the releasing beam is delivered via the imaging path. This scheme facilitates alignment through the pupil and enhances reliability. The reliability stems from the fact that, by viewing the image on the fundus and optimizing it, one centers the imaging path in the pupil.

The coupling of an argon laser 32 to the fundus camera 31 is achieved, as shown in the Figure, at the conjugate image plane originally used for the eyepiece. The argon laser 32 is fed into a fiber by a laser to fiber coupler 1. The fiber is one of the arms of a fused fiber optic coupler 2 which channels part of the power toward colliminating lens 8. The fiber output is collimated, projected on the conjugate plane of the retina and directed into the imaging path by a dichroic filter 11 reflecting blue (488 nm). The focal length of the colliminating lens 8 and the numerical aperture of the fiber are chosen to yield the desired beam spot on the retina. The dichroic filter 11 maximizes the amount of light directed toward the eye while minimizing the reflected light reaching a charge-coupled-device (CCD) camera 33. The reflected blue light reaching the CCD camera 33 is further reduced by green band pass filter 12 used also in fluorescein angiography to block the excitation and pass the fluorescence. The image of the fundus is demagnified and focused on the CCD camera 33 with the aid of lens assembly 13.

To visualize the beam during alignment, an infrared light source 6 is added coaxially to the fiber via the fused fiber optic coupler 2. The image of the beam exiting the delivery assembly 34 is visualized on a monitor. The beam is directed to different regions on the fundus by moving the location of delivery assembly 34 on the conjugate plane. The position of this assembly is adjusted by a motorized translation stage 35 attached to the body of fundus camera 31 and controlled via computer by a joystick.

The power of the laser is measured at a conjugate plane of the pupil by the light partially reflected by a thin glass 19 toward a focusing lens 20 and a photosensor 21. The size of the mirror matches the diameter of the aperture to restrict the measurement to the part of the beam that is directed into the eye.

The laser pulse for liposome release is controlled by a computer controlled shutter 9. A hard-wired fixed-delay shutter 22 prevents accidental long exposures in case of computer malfunction.

EXAMPLE 1.2

Delivery of Illumination Beam

The blue light illumination necessary for angiographic visualization is presently delivered through a fiber assembly replacing the original flash unit. This arrangement is adequate for large pupils but can cause losses in smaller animals with pupils that are narrower than the annulus of light.

The illumination beam originates from the second arm of the fiber coupler splitter 2 fed by the argon laser 32. The pulse duration is determined by the laser internal shutter under the control of the computer. The output of the fiber illuminates, via a collimating lens 3, the conjugate image plane of the retina and is placed at a plane conjugate to the pupil. By forming a small spot at the pupil the beam eases the alignment into the pupil.

EXAMPLE 1.3

Operation of the System

The operation of the system is synchronized through a computer with the aid of a program written with virtual instrumentation software. The camera signal is used for the synchronization. Upon activation by a foot pedal, the video recorder is started, the location on tape is recorded in a file, the argon laser 32 is turned on, the releasing beam delivery shutter 22 is opened for a given period and, after a preset delay, the illumination is turned off followed by the video recorder.

EXAMPLE 1.4

Image Acquisition

The images first are acquired on a Betacam video recorder. The video recorder can be replaced by a frame grabber capable of recording 24 Mbytes of images. This allows spanning of a sequence of 3 seconds at a rate of 16 images per second. After each delivery, the data can be compressed and stored on an optical drive.

Unless the images are digitized on line, they can be retrieved for analysis from the video tape. The playback of the video recorder is controlled by the computer. The digital locations on tape, recorded during the experiment, permit selection of a given sequence and digitize it in parts with the current frame grabber equipped with 4 Mbytes of memory.

EXAMPLE 1.5

Image Processing

The most basic routine consists of subtracting the angiogram immediately preceding the release from the sequence following the liposomes release. This permits isolation of the dynamic changes. There is little motion during a sequence and no need for registration.

Once the static background has been subtracted, a number of image enhancement algorithms can be applied. As mentioned above, flow in the CNV is slower than that in the normal tissue. Thus, it is feasible to differentiate between the clearance rate in the normal choriocapillaris from that in the CNV. Windows of interest, placed in different regions of the image, are used to plot the intensity versus time and measure the decay rate. A distribution curve of the decay rates in the different windows can thereby be generated. Since the clearance of the choriocapillaris is relatively homogeneous in the posterior pole, one can obtain a distribution of clearance rates with a sharp peak at a high value, corresponding to the normal areas, well separated from the distribution of lower rates due to the CNV. Experience permits the identification of a reliable cutoff to isolate the CNV clearance rates. This then yields a time in the sequence after which the remaining fluorescence is only in sluggish vessels, namely in the CNV. The frames from this time on are then combined to yield a map of the CNV. The reliability of this or alternative algorithms can be verified by comparisons with histology.

EXAMPLE 2

Reagent Preparation

Liposomes were prepared in accordance with standard techniques using two lipids, DPPC and DPPG (Avanti Polar Lipids, Pelhan, Ala.) without further purification to generate liposomes with a phase transition of 41° C. Examples relating to the use of liposomes for delivery of substances in the mammalian body are disclosed in U.S. Pat. No. 4,310, 506; 4,350,676; 4,515,736; 4,522,803; 4,610,868; 4,891, 043; and 5,257,970, the disclosures of which are herein incorporated by reference. Large unilamellar vesicles were obtained by reverse-phase evaporation using art-recognized techniques such as those described by Magin et al. (1984) 34 *Chem. Phys. Lipids* 245–256, or forced extrusion following freeze-thaw cycles as described by Hope et al. (1985) 812 *Biochem. Biophys. Acta* 55–65. The mean diameter of the liposomes was measured by light scattering (Nicomp, Goleta, Calif.). Liposomes occupied only a fraction of the volume in the preparation. 6-Carboxyfluorescein (Molecular Probes, Junction City, Oreg.) was purified on a hydrophobic column and diluted to approximately 100 mM using art-recognized techniques such as those described in Zeimer et al. (1988) 29 *Invest. Opthalmol. Vis. Sci.* 1179–1183. A sufficient dose for baboons weighing 9 to 12 kg is approximately 14 mg/kg; typically the concentration was 13.3 mM. This corresponds to a 1.5 ml/kg dose of liposome suspension injected intravenously. The concentration of the dye encapsulated in the liposomes was tested by measuring the fluorescence of the dialyzed preparation before and after lysis with detergent. The measured concentration is compatible with the release of the original 100 mM concentration if the liposomes occupy one seventh of the volume. This concentration is well within the range of concentrations that cause fluorescence quenching. On release in the plasma, the dye was diluted and fluoresced strongly.

As will be understood by the skilled practitioner, fluorescent substances suitable for use in the instant invention include those which are suitable for administration to mammals, including humans. It will be further understood that fluorescent substances amenable to encapsulation, or which can be rendered amenable to encapsulation are suitable for use in the instant invention. Moreover, substances whose fluorescence is quenched when in an encapsulated form at an appropriate concentration as described herein also are suitable for use in the methods and materials of the instant invention. Thus, dyes such as 6-carboxyfluorescein and similar fluorescein derivatives are suitable for use herein. Particularly useful fluorescent substances are those which can be excited by and can emit light at wavelengths not strongly absorbed by opaque tissue lesions, blood and/or biological pigments. Such fluorescent substances readily can be detected in vivo in the presence of biological opacities. In this regard, indocyanine green (ICG) also is suitable because its excitation is not strongly absorbed by opacities, blood, or ocular pigments. Similarly, aluminum phthalocyanine tetrasulfonate (AlPcS$_4$) is an exemplary fluorescent substance and tissue-reactive agent for the reasons discussed herein below, however, other equivalent substances would also be suitable. Identification of equivalents is well within the skill of the ordinary practitioner and would require no more than routine experimentation.

Similarly, aluminum phthalocyanine tetrasulfonate (AlPcS$_4$) is presented as an exemplary fluorescent dye and tissue-reactive agent for the reasons discussed below, however, other equivalent dyes would also be suitable for use in the instant invention. Again, identification of equivalents is well within the skill of the ordinary practitioner and would require no more than routine experimentation.

Aluminum phthalocyanine tetrasulfonate (AlPcS$_4$) is well-known in the art (see, for example, U.S. Pat. No. 5,166,197, the disclosure of which is herein incorporated by reference) and is considered useful as a tissue-reactive agent because its peak absorption around 675 nm assures penetration through blood (only 11% absorption by a 100 micron layer). Further, it is water soluble and can be encapsulated efficiently. It has one of the highest known absorption coefficients (30 times higher than that of hematoporphyrin derivatives) ensuring high sensitization with minimal amount of light on the retina. It is a well-defined compound which can be synthesized with high purity. Finally, it is removed within 24 hours from the blood thereby reducing the period of light sensitivity which has been a significant limitation of other photosensitive agents. This tissue-reactive, photosensitive agent has been demonstrated to be non-toxic in a number of species and no side effects have been reported when it was used intraperitonially in a few patients.

Aluminum phthalocyanine tetrasulfonate (Porphyrin Products, Logan, Utah) can be stored at 20° C. in the dark in the powder form. It is dissolved in sterile water for injection and filtered through a 0.2 micron syringe filter. Liposomes of the instant invention are prepared following methods well-known in the art such as those described in detail previously by Zeimer et al. (1988) 29 *Invest. Ophthalmol. Vis. Sci.* 1179–1183.; Zeimer et al. 30 *Invest. Ophthalmol. Vis. Sci.* 660–667; and, Hope et al. (1985) 812 *Biochem. Biophys Acta* 55–65. Dipalmitoylphosphatidyl-choline (DPPC) and dipalmitoylphosphatidyl-glycerol (DPPG) were obtained from Avanti Polar Lipids (Pelham, Ala.) and used without further purification.

Raw materials were tested to ensure their sterility and glassware was autoclaved. Liposomes were prepared using standard methods and aseptic techniques and tested for sterility by incubating them at 37° C. on blood agar plates and in thioglycollate media for 72 hours using standard materials and methods. The art-recognized limulus amebocyte lysate (LAL) test was used to ensure that the liposomes and water were essentially free from pyrogens, especially endotoxins. Since the size distribution of the liposomes affects their half-life in the blood stream and since particles greater than 5 microns could cause clotting, the liposome preparation was filtered through a 0.4 micron polycarbonate filter using standard materials and methods. The integrity of the liposomes was monitored by verifying that the concentration of the unencapsulated substance increased significantly after exposure of liposomes to detergent.

EXAMPLE 3

Regulation of the Primate Retinal Microcirculation

Understanding the regulation of the retinal microcirculation is important, because there is evidence that, in most vascular diseases, the earliest pathology occurs at the capillary level. The capillary beds in the retina next to the fovea are organized in two basic layers; a deep one, in the inner nuclear layer, and a more superficial one, in the ganglion cell and nerve fiber layer. A more detailed examination has revealed a further subdivision into four layers closely matching the thickness of different neuronal layers and indicating a link between metabolic demand and the arrangement and density of the microvasculature. The multilayer arrangement leads to a plexus of numerous capillaries fed by a single relatively large arteriole. Consequently, the retinal microvasculature is subjected to a large pressure head, and changes in its resistance are likely to play a significant role in blood flow regulation.

Laser-targeted angiographic methods of the instant invention were applied to study the response of the macular circulation to physiological challenges. The local metabolic demand was increased by flickering of light, a stimulus which has been shown to induce blood flow changes. The illumination was chopped and within 10 seconds following the end of the flicker, a sequence of three laser-targeted angiograms was obtained. Three baboons were used in the study and the measurements were performed on two occasions in each animal. The arterial transit time, the capillary transit time and the fluorescence intensity of each capillary bad were measured. In response to flicker, the blood flow in retinal arteries increased by 30%. The response of the microcirculation was not homogeneous. It showed a maximum increase in the mid perifoveal region where there is an increase in ganglion cells and nerve fibers. The maximum change in the index representing capillary blood flow exceeded ($p<0.08$) the change in the blood flow in the artery. It appears that, in response to an increased metabolic demand, a redistribution of blood occurs in the retina whereby more blood is directed to the inner (superficial) capillary layer which is provided with an apparently lower resistance due to its architecture. This regulation would be beneficial in preserving the supply to the inner tissues, which consist of neuronal tissue remote from the choroid.

The application of laser targeted angiography as performed using methods of the instant invention permitted, for the first time, the study of the local regulation of the retinal microcirculation. The results indicate that the regulation is intimately coupled to the specific demand of the tissue it perfuses and thus varies across the macula and the depth of the retina.

EXAMPLE 4

Visualization and Hemodynamics of the Non-Human Primate Choriocapillaris

Limited information is available on the physiology and pathophysiology of the choroidal microvasculature, mainly due to the difficulty in visualizing it in vivo. Conventional fluorescein and even indocyanine green angiography are limited by the fluorescence emitted from the large choroidal vessels which dominate the angiographic image and hinder visualization of the faint fluorescence from the thinner choriocapillaris. While a technique based on the subtraction of consecutive dynamic angiograms has minimized this large background (Flower (1993) 34 *Invest. Ophthalmol. Vis. Sci.* 2720–2729), visualization still depends on an ill-defined feature relating to the relative dynamics of vascular beds. The fact that slowly perfused ones may not be imaged is a significant limitation. In addition, conventional intravenous injection of dyes yields an ill-defined dye front, must be limited to few boli, and cannot be synchronized with the cardiac cycle.

Using the materials and methods of the instant invention, laser-targeted angiography for visualizing the choroidal microvasculature in non-human primates has been accomplished. The local release of dye from the heat-sensitive liposomes in the choroidal arteries was carried downstream and generated a dye front which reached the choriocapillaris. An intense and predominant fluorescence from the choroid was observed in the absence of significant retinal fluorescence. The contribution of the choriocapillaris to the image was dominant compared to that of the deep choroidal vessels. Of particular notice was the lack of released dye in the retinal vasculature and the dominant contribution of the choriocapillaris to the angiographic image compared to that of the deep choroidal vessels. The dynamic angiograms obtained in accordance with the methods of the instant invention revealed the filling and emptying of the choriocapillaris lobules. The dye was first cleared out at the center of polygon-shaped areas and disappeared radially to form a hypofluorescent zone surrounded by a polygonal outline. The filling and clearing pattern of the choroidal microcirculation was unchanged during the different phases of the cardiac cycle. This pattern of filling and clearing resembles the one described by Hayreh (1974) *Graefes Arch. Clin. Exp. Ophthalmol.* 165–179, and substantiates the concept of choroidal lobules each supplied at its center by an arteriole and drained by annular venous channels as described by Torcyzynski et al. (1976) 81 *J. Ophthalmol.* 428–440 and Yoneya (1987) 105 *Arch. Ophthalmol.* 681–687. Since anatomically the choriocapillaris forms a continuous bed, the segmental pattern revealed by the laser-targeted angiography method of the instant invention must be attributed to the dynamics of the circulation. This pattern can be explained by the presence of a pressure gradient between the central arteriole and the surrounding venules which forces flow from the arterioles into the venules and prevents flow into the adjacent network of capillaries. The average size of the lobules (n=76) was 270±90 $\mu$m in diameter. Adjacent arteries typically supplied neighboring clusters which fit together like a jig-saw puzzle. A feeding artery often supplied remote islands of the choriocapillaris. Alternatively, clusters were observed with unfilled areas. The minimal lateral diffusion of the dye indicates that there is no dynamic communication between adjacent clusters under physiologic conditions.

As further evidence of the extent of the present invention's successful visualization, a choroidoretinal scar was created by delivering a high power laser pulse over a large (one disc diameter) area of the posterior pole with the ND:YAG laser. A conventional fluorescein angiogram was dominated by hyperfluorescence at the margin of the lesion and by hypofluorescence at the center of the scar. The angiogram did not provide any information on the underlying choroidal vasculature. In contrast, the laser-targeted angiograms of the instant invention revealed perfused clusters of choriocapillaris both in the region of the hyperfluorescence and at the center of the scar. The results demonstrate that thin nets of subretinal vessels, such as the choriocapillaris, can be visualized in non-human primates by the laser-targeted angiography method of the instant invention while conventional fluorescein angiography does not provide any clinically-useful information.

EXAMPLE 5

Visualization of CNV

A rat model of a CNV-type lesion was created by heavy laser burns following a well-established protocol such as the one described by Dobi et al. (1989) 107 *Arch. Ophthalmol.* 264–269. Although the choroidal nature of the newly-formed vessels resulting from such a protocol has been previously documented, histology was performed to confirm that the new vessels were located above Bruch's membrane as in human CNV. To highlight patent vessels, the histological method of Kues et al. was used as described in 13 *Bioelectro.* 379–393 (1992). This method involves infusing the animal with horseradish peroxidase (HRP) prior to sacrifice, embedding the appropriate section of the eye in plastic using standard techniques and subsequently reacting with diaminobenzidine the HRP in the 2 micron histologic sections using art-recognized histological protocols. This yields an orange staining in patent vessels, i.e., those open to blood flow. Histology of the periphery of a burn demonstrates that the new, CNV-type vessels are close to the choriocapillaris, thus resembling human CNV. Retinal pigment epithelian (RPE) cells were seen covering the CNV. The choroidal nature of these vessels was further confirmed in another section of the same lesion by observing their connection to the choroid through the Bruch's membrane. In this embodiment of the instant invention, the photosensitive agent was released locally by a laser pulse and also activated to cause the release of free radicals.

The CNV-type lesions were then studied with conventional fluorescein angiography and the laser-targeted angiography method of the instant invention. In the case of "classic" CNV, so defined by a well-delineated leakage of dye on conventional fluorescein angiography, laser-targeted angiography yielded far superior visualization of the CNV-type lesion. Using laser-targeted angiography, the dye highlighted the normal choriocapillaris as well as the abnormal pattern of CNV vessels. The normal choriocapillaris cleared rapidly while the CNV revealed a sluggish flow. These results provide experimental proof that, at least in this model, CNV has an abnormal slow flow. The sluggish flow also caused less dilution of the dye and thus yielded a bright fluorescence. The rapid clearance of the normal choroid had the dramatic effect of leaving the CNV clearly delineated. In addition to delineation of the CNV, laser-targeted angiography revealed the dynamics of the flow in the CNV. The origin of the flow, namely localization of the local feeding vessels, could be identified clearly and the drainage of the dye into the surrounding normal choroid provided evidence that these pathological vessels were of choroidal origin thus confirming their classification as a CNV.

Finally, the data indicated that multiple liposome releases—even in a CNV shown to leak on conventional fluorescein angiography—do not cause accumulation of dye such that the visualization is impaired. Fluorescein angiography performed at 14 seconds and 2 minutes after injection revealed the presence of a lesion with progressive leakage which is typical of "classic" CNV. A lack of sharp delineation of the CNV was observed. Live video images indicated that the leakage was localized below the neurosensory retina. In contrast, laser-targeted angiography revealed a CNV with an exact location and flow pattern. Angiograms obtained 17, 165 and 560 msec after the end of the dye release, respectively, depicted a brightly fluorescent abnormal pattern of vessels and diffusely fluorescent patches. The abnormal pattern of the brightly fluorescent vessels is typical of a CNV. The diffuse patches which evolved rapidly correspond to the choriocapillaris. The same lobular pattern was observed in regions devoid of lesions. An angiogram obtained at 2 seconds showed that the fluorescent dye cleared from the choriocapillaris while it remained in the CNV, indicating a sluggish flow. The advance of the dye clearly delineated the direction of flow in the CNV. Subsequent releases in other regions of the CNV revealed a similar pattern of flow thus demonstrating its anatomical nature. Additionally, although the angiograms were obtained after seven previous releases performed within five minutes, there was no significant accumulation of dye and no deterioration in visualization. The pre-release image was subtracted from the subsequent images to highlight the dynamic changes.

In a case of "occult" CNV, so defined by the lack of leakage or by an ill-defined area of leakage on conventional fluorescein angiogram, laser-targeted angiography clearly delineated a CNV and its flow pattern in a manner similar to that of the above-described "classic" case. Fluorescein angiograms obtained at 29 seconds and 78 seconds after injection revealed the presence of patchy fluorescence which did not evolve with time providing no indication of the presence of a CNV. In contrast, laser targeted angiography revealed a CNV with its exact location and flow pattern. Angiograms obtained 50, 110 and 430 msec after the end of the dye release, respectively, depicted a brightly fluorescent abnormal pattern of vessels and fluorescent patches. The abnormal pattern of the brightly fluorescent vessels is typical of a CNV. The patches evolved rapidly into a lobular pattern characteristic of choriocapillaris. Laser-targeted angiography at 1.2 seconds showed that the fluorescent bolus cleared from the choriocapillaris while it remained in the CNV, indicating a sluggish flow. Subsequent releases in other regions of the CNV revealed a similar pattern of flow thus demonstrating its anatomical nature.

Thus, this application of laser-targeted angiography to release dye in the choroid yielded unique angiograms of the choriocapillaris and demonstrated that laser-targeted angiography is a powerful tool for physiological studies of this vascular tissue. Laser-targeted angiography is a tool of choice to study the patency or flow of the choriocapillaris in diseases which may well be due to early pathologies of the choriocapillaris such as choroideremia, gyrate atrophy, and acute placoid multifocal pigment epitheliopathy.

The most significant implication of these results is that laser-targeted angiography in accordance with the instant invention is useful for the diagnosis of ARMD-related CNV. Laser-targeted delivery supplies information currently unavailable. The CNV can be delineated in "classic" and "occult" cases alike, thus demonstrating that laser-targeted angiography is not dependent, like conventional angiography, on leakage from the CNV. In addition, the identification of the origin of the flow allows treatment of feeder vessels.

EXAMPLE 6

Targeted Occlusion of Vessels

EXAMPLE 6.1

Laser-Targeted Occlusion in Iris Vessels: Rodent

Laser-targeted occlusion depends on the discovery disclosed herein that a tissue-reactive or photosensitive agent may be activated during its very short presence in the vessel lumen after its release from the heat-sensitive liposomes. In this example, a photosensitive agent, aluminum phthalocyanine tetrasulfonate ($AlPcS_4$,) was used because its peak absorption around 680 nm assures penetration of fluorescence through blood (only 11% absorption by a 100 gm layer). This and other advantages of $AlPcS_4$ over other photosensitizing agents have been discussed above. Photosensitive agents such as $AlPcS_4$ are well-known in the art (see, for example, U.S. Pat. No. 4,889,129 and 5,166,197, the disclosures of which are herein incorporated by reference).

To demonstrate that the method of laser-targeted occlusion of the instant invention can occlude vessels, a customary model which yields art-recognized and unequivocal documentation of its efficacy was used. The iris vessels of the albino rat are considered the model of choice because they are readily visible and untreated portions could be used as well-defined and stable controls. It is within the skill of the ordinary practioner to modify the experimental conditions described herein to extend the methods of the instant invention to a pigmented eye. The principles exemplified by the rat model are applicable to non-human primate and human subjects. The protocol now described was designed in accordance with the ARVO Resolution on the Use of Animals in Research. The experiments were conducted on six albino male Sprague Dawley rats weighing 250 to 300 gm. They were anesthetized with ketamine (50 mg/kg) and xylazine (10 mg/kg) intramuscularly.

Ideally, the activation of the photosensitizer can be performed at the maximal absorption of 675 nm. In this example, the same laser used for raising the temperature of the tissue to cause release of the dye and agent from liposomes was used to activate the agent. A dye laser (Coherent, Palo Alto, Calif.), operated at 577 nm, was chosen to match the high absorption of blood at this wavelength thereby raising the temperature of the iris vessel efficiently. The laser was coupled to a slit lamp biomicroscope as part of an ophthalmic laser delivery system.

The power of the laser was set according to calculations similar to those used by other skilled practitioners for the power necessary to warm by 4° C. blood vessels embedded in a transparent medium. (See, for example, Bebie et al. (1974) 52 *Acta Ophthalmol.* 13–36.) This temperature rise is sufficient to release the contents of the heat-sensitive liposomes. The power of the laser spot was 50 mW and its diameter was 400 mm.

Prior to the injection, the irides of both eyes were imaged to obtain a baseline. The liposome preparation was injected intravenously to yield a dose of $AlPcS_4$ of 7.5 mg/kg. A portion of the iris, corresponding to 2 clock hours, was treated. The number of pulses necessary to obtain an effect was determined by pilot experiments. To control for the effect of the laser by itself, the left iris was exposed to the laser prior to the injection of the photosensitive dye. The dye was then injected and the right iris was treated within 5 minutes of injection, although treatment can occur as early as practically feasible post-injection.

The heat-sensitive liposomes of the instant invention may release some of their content (10 to 15%) at body temperature. To assess the effect of this unencapsulated portion of the dose, a second control was performed. The same liposome preparation was lysed by heating it beyond the phase-transition and 20% of the dose of the lysed preparation was administered to another rat. The iris was then treated within 5 minutes of the injection with the same laser parameters as above. The iris was continuously visualized for 15 minutes to detect any change in the vessels. To control for potential individual variability the treatment was followed 20 minutes later by an injection, to the same animal, of intact liposomes and a different quadrant was treated with the same laser delivery protocol.

The eyes were followed-up by obtaining red-free video images with a CCD Camera (Texas Instruments) coupled to one of the viewing arms of the slit lamp biomicroscope. The video output was recorded on magnetic tape with a high frequency videorecorder (Sony, Tokyo, Japan) and later digitized with a frame grabber (Epix, Northbrook, Ill.

Using 4 animals, its was established that 40 pulses of 0.5 sec yielded visible results. These parameters were thus adopted for the rest of th e studies.

When the right eye was occluded after liposome injections, vessel engorgement followed by vessel spasms, hemorrhages and local iris tissue expansion were observed upon the delivery of 20 pulses. Local iris tissue constriction then occurred at the end of 40 pulses. In contrast, in the left control eye treated prior to liposome injection, no effect was noticed in the blood vessels or the iris tissue during the delivery.

The follow-up examinations with red-free imaging revealed, in the treated eye, hemorrhages which cleared within a week, leaving the iris tissue with non-perfused vessels. At 25 days, the occluded vessels in the treated area could be seen as non-perfused vessels (ghost vessels). During the follow-up period which was done monthly for 8 months, no reperfusion of occluded vessels was observed. In contrast, the follow-up of the control eye did not reveal any ophthalmoscopically visible pathology at any time point.

In the second experiment, following the injection of the photosensitizer at 20% of the encapsulated dose, no response was observed in the blood vessels or the pupil when observed for fifteen minutes following completion of 40 deliveries. When the intact liposome preparation was injected in the same animal and another quadrant was treated, the occlusive events mentioned above were observed after the first 20 pulses.

The results demonstrate the success of laser-targeted occlusion performed in accordance with the methods of the instant invention. The control experiments did not yield the effects which were observed when the photosensitive agent was released at high concentration from the liposomes and simultaneously irradiated. This assures that the occlusion was not due to the direct effect of the laser on the tissue or to the activation of the low dose of free photosensitizer. In contrast, the treatment caused occlusion which lasted for the long term follow-up. The fact that ghost vessels were visible from the seventh day onwards provides conclusive evidence that the observation of lack of perfused vessels was due to occlusion and not to artifacts such as overlying edematous fluid or exudate.

These results reveal that, photosensitizers can yield occlusive effects when activated during their presence inside the blood stream. Due to the short passage of the agent, the activated photosensitive agent did not have sufficient time to exit the lumen. This sheds some light on one of the mechanisms of photodynamic therapy as it indicates that the penetration of the photosensitizer into the tissue or the cells is not a prerequisite for its effect.

But, most importantly, this study illustrates successful occlusion with the instant invention's method of laser-targeted occlusion. The success in occluding vessels in the iris is significant because these are subjected to a high pressure head. Moreover, abnormal new vessels such as those encountered in macular degeneration are likely to be prone to even more damage due to their defective endothelial lining.

EXAMPLE 6.2

Laser-Targeted Photo-Occlusion in Choroidal Vessels: Rodent

To demonstrate that the retina can be preserved while occluding the choroid, experiments were performed in the choroid in pigmented rats. Liposomes with $AlPcS_4$ were injected, their content was released locally by the laser pulse and the area was simultaneously irradiated to activate the $AlPcS_4$. Fluorescein angiography was performed within two hours after the treatment, and revealed a slow filling and subsequent leakage of treated vessels in the choroid. These sypmtoms are indicative of a fresh occlusive event. In contrast, the retinal capillaries were clearly unaffected as illustrated by their perfusion and lack of leakage. Camera motions in live video images provided depth resolution which clearly indicated that the leakage was localized at the choroidal level. The retinal capillaries overlying the treated area did not sustain damage as demonstrated by their similarity to those in the untreated area. The animal was sacrificed 2½ hours after the treatment and histology was performed as described previously. The time was selected to precede secondary damage to the RPE and photoreceptors likely to occur within 2 to 3 days following ischemia in the choriocapillaris. There was a dramatically reduced presence of HRP in the choroid at the treatment site compared with heavy staining in the control area. Most importantly, no damage was present in the RPE, photoreceptors and neuro-retina. These results clearly indicate that laser-targeted occlusion is not accompanied by the devastating damage observed immediately after laser photocoagulation.

The clinical impact of a safe method to occlude CNV is significant The success in occluding normal vessels in the iris which are subjected to a high pressure head, indicates that laser-targeted photo-occlusion is a successful method of occlusion. Moreover, the success in occluding the normal choroid without damage to the RPE, photoreceptors and outer neuro-retina, documented angiographically as well as histologically, clearly demonstrate that the method of the instant invention provides an approach that can prevent the devastating injury induced by laser photocoagulation.

EXAMPLE 6.3

Laser-Targeted Occlusion: Primates

A model of CNV can be created following protocols, each of which is well-established and familiar to the skilled practitioner. See, for example, Ryan (1982) 100 *Arch. Ophthalmol.* 1804–1809 and Miller et al. (1993) 111 *Arch. Ophthalmol.* 855–869. The presence of CNV will be determined by laser-targeted angiography. In eyes with two or more lesions with CNV, one lesion will be left as a control and the others will be subject to laser-targeted photo-occlusion. The assignment will be made by an independent observer.

The follow-up with red-free fundus images, laser-targeted angiography, and fluorescein angiography will be done weekly until the vessels in the control areas begin their normal regression. The animals will then be sacrificed and the eyes will be subject similarly to histology.

It is anticipated that laser-targeted occlusion will provide a safe method to occlude CNV in primates and that essentially no damage to the RPE, photoreceptors and outer neuro-retina will be documented both angiographically and histologically.

Laser-targeted occlusion as described herein can provide a therapy that can surpass laser photocoagulation and conventional photodynamic therapy for a variety of reasons. For example, the results of the specific visualization of the choroidal vasculature indicate that the tissue-reactive or photosensitive agent can be released in the subretinal vasculature while avoiding release in the retinal capillaries. Thus these vessels will not be damaged during the irradiation to activate the agent. Moreover, by irradiating immediately following release from the liposomes, the damage can be limited to the vessels perfused. Accumulation of the agent in the interstitial tissues and subsequent damage upon irradiation can be avoided. Additionally, CNVs are perfused by a slower flow than the normal choriocapillaris. The tissue reactive or photosensitive agent can be released and the tissue irradiated only after enough time has elapsed to ensure clearance from the normal choriocapillaris. This ensures preservation of the choriocapillaris which is crucial to the maintenance of the retinal pigment epithelium. Furthermore, nonthermal occlusion avoids extensive scarring and breaks in Bruch's membrane believed to increase the recurrence risk of neovascularization. Finally, laser targeted occlusion will benefit a large portion of the population with macular degeneration by providing selective occlusion with better preservation of vision.

EQUIVALENTS

The invention may be embodied in other specific forms without departing from the spirit or essential characteristics thereof. The foregoing embodiments are therefore to be considered in all respects illustrative rather than limiting on the invention described herein. For example, laser-targeted occlusion of vasculature can be practiced according to the foregoing methods in body tissues other than the mammalian eye. Scope of the invention is thus indicated by the appended claims rather than by the foregoing description, and all changes which come within the meaning and range of equivalency of the claims are therefore intended to be embraced therein.

What is claimed is:

1. A diagnostic reagent for visualizing a blood vessel or blood sinus in a mammal and useful to form a medical reagent for occluding a blood vessel or blood sinus, the diagnostic reagent comprising:
   (a) a fluorescent dye encapsulated within a heat-sensitive liposome, the fluorescent dye being releasable from the heat-sensitive liposome at a temperature above mammalian body temperature; and
   (b) a pharmaceutically-acceptable vehicle,
   wherein said diagnostic reagent is suitable for systemic administration to said mammal and is combinable with an agent selected from the group consisting of a tissue-reactive agent and a tissue-specific factor, thereby to form a medical reagent for chemically occluding a blood vessel or blood sinus.

2. The diagnostic reagent of claim 1 wherein the fluorescent dye is present in the heat-sensitive liposome at a quenching concentration.

3. The diagnostic reagent of claim 1 wherein the fluorescent dye is releasable from the heat-sensitive liposome at a temperature of about 41° C.

4. The diagnostic reagent of claim 1 wherein the fluorescent dye is water-soluble.

5. The diagnostic reagent of claim 1 wherein the heat-sensitive liposome has a phase transition of 41° C.

6. The diagnostic reagent of claim 1 wherein the heat-sensitive liposome is unilamellar.

7. The diagnostic reagent of claim 1 wherein the heat-sensitive liposome is less than about 450 nm in diameter.

8. The diagnostic reagent of claim 1 wherein the heat-sensitive liposome is not more than about 450 nm in diameter.

9. The diagnostic reagent of claim 1 wherein the heat-sensitive liposome comprises dipalmitoylphosphatidylcholine.

10. The diagnostic reagent of claim 1 wherein the heat-sensitive liposome comprises dipalmitoylphosphatidylglycerol.

11. The diagnostic reagent of claim 1 further comprising a tissue-specific factor.

12. The diagnostic reagent of claim 1 wherein the fluorescent dye is 6-carboxyfluorescein.

13. The diagnostic reagent of claim 1 wherein the fluorescent dye is indocyanine green.

14. A medical reagent for chemically occluding a blood vessel or blood sinus in a mammal, comprising:
   (a) the diagnostic reagent of claim 64; and
   (b) a tissue-reactive agent effective to cause chemical damage to tissue upon activation.

15. The medical reagent of claim 14 wherein the tissue-reactive agent is encapsulated in a heat-sensitive liposome.

16. The medical reagent of claim 14 wherein the tissue-reactive agent and the fluorescent dye are co-encapsulated within a heat-sensitive liposome.

17. The medical reagent of claim 14 wherein the tissue-reactive agent is the fluorescent dye.

18. The medical reagent of claim 14 wherein the tissue-reactive agent is a photosensitive agent effective to cause chemical damage to tissue upon activation.

19. The medical reagent of claim 14 wherein the tissue reactive agent comprises aluminum phthalocyanine tetrasulfonate.

20. A kit for visualizing and chemically occluding a blood vessel or blood sinus in a mammal, comprising:
   (a) a fluorescent dye encapsulated within a heat-sensitive vesicle, the fluorescent dye being releasable from the heat-sensitive vesicle at a temperature above the body temperature of said mammal; and
   (b) a tissue-reactive agent effective to cause chemical damage to tissue upon activation.

21. The kit of claim 20 wherein the fluorescent dye is water-soluble.

22. The kit of claim 20 wherein the fluorescent dye is present in the heat-sensitive vesicle at a quenching concentration.

23. The kit of claim 20 wherein the fluorescent dye is releasable from the heat-sensitive vesicle at a temperature of about 41° C.

24. The kit of claim 20 wherein the heat-sensitive vesicle has a phase transition of 41° C.

25. The kit of claim 20 wherein the heat-sensitive vesicle is a unilamellar vesicle.

26. A kit for visualizing and chemically occluding a blood vessel or blood sinus in a mammal, comprising:
   (a) a fluorescent dye;
   (b) a tissue-reactive agent effective to cause chemical damage to tissue upon activation; and,
   (c) a reagent comprising an encapsulant, wherein the fluorescent dye is introducible to the encapsulant to form a heat-sensitive vesicle comprising the encapsulant and the fluorescent dye, wherein the fluorescent dye is releasable from the heat-sensitive vesicle at about 41° C.

27. The kit of claim 26, wherein the fluorescent dye is introducible to the encapsulant to form a heat-sensitive vesicle less than about 450 nm in diameter.

28. The kit of claim 26, wherein the fluorescent dye is water-soluble.

29. A method of diagnosing a vascular abnormality in a mammalian eye, the method comprising the steps of:

(a) administering the diagnostic reagent of claim 1 to a mammal;

(b) selectively heating vasculature at a pre-determined anatomical locus within the eye such that a heat-sensitive liposome present at the locus releases the fluorescent dye; and (c) monitoring clearance of the fluorescent dye from vasculature at the locus with normal blood flow, while simultaneously monitoring and visualizing persistence of the fluorescent dye within vasculature at the locus having subnormal blood flow, thereby to identify a vascular abnormality having subnormal blood flow.

* * * * *

UNITED STATES PATENT AND TRADEMARK OFFICE
CERTIFICATE OF CORRECTION

| | |
|---|---|
| PATENT NO. | : 6,440,950 B1 |
| APPLICATION NO. | : 09/676832 |
| DATED | : August 27, 2002 |
| INVENTOR(S) | : Zeimer |

It is certified that error appears in the above-identified patent and that said Letters Patent is hereby corrected as shown below:

In claim 14, line 3, please delete the claim reference numeral "64" and please insert and substitute in its place --1--.

Signed and Sealed this

Twenty-ninth Day of August, 2006

JON W. DUDAS
*Director of the United States Patent and Trademark Office*